United States Patent [19]

Gubelmann et al.

[11] Patent Number: 5,055,623
[45] Date of Patent: Oct. 8, 1991

[54] PREPARATION OF PHENOLS BY DIRECT $N_2O$ HYDROXYLATION OF AROMATIC SUBSTRATES

[75] Inventors: Michel Gubelmann, Lyon; Jean-Michel Popa, Drancy; Philipe-Jean Tirel, Oullins, all of France

[73] Assignee: Rhone-Poulenc Chimie, Courbevoie, France

[21] Appl. No.: 541,956

[22] Filed: Jun. 22, 1990

[30] Foreign Application Priority Data

Jun. 22, 1989 [FR] France ................... 89 08582

[51] Int. Cl.$^5$ ............................................. C07C 37/60
[52] U.S. Cl. ........................ 568/800.00; 568/754; 568/771
[58] Field of Search ............... 568/800, 650, 771, 754

[56] References Cited

FOREIGN PATENT DOCUMENTS

| 0341165 | 11/1989 | European Pat. Off. ............ 568/800 |
| 102632 | 12/1974 | Japan .................................. 568/800 |
| 0184036 | 9/1985 | Japan .................................. 568/800 |
| 1236738 | 10/1986 | Japan .................................. 568/800 |
| 2067038 | 3/1987 | Japan .................................. 568/800 |

*Primary Examiner*—Werren B. Lone
*Attorney, Agent, or Firm*—Burns, Doane, Swecker & Mathis

[57] ABSTRACT

Phenol/substituted phenols are prepared by directly hydroxylating an aromatic substrate with nitrous oxide, in vapor phase, in the presence of a modified (acidified) ZSM-5 or ZSM-11 zeolite, containing such elements as Ga, Fe, B, In, Cr, Sc, Co, Ni, Be, Zn, Cu, Sb, As or V.

13 Claims, No Drawings

PREPARATION OF PHENOLS BY DIRECT N₂O HYDROXYLATION OF AROMATIC SUBSTRATES

BACKGROUND OF THE INVENTION

1. Field of the Invention

The present invention relates to the preparation of phenol or a substituted phenol, and, more especially, to the preparation of phenol/substituted phenols, by the catalytic hydroxylation of aromatic substrates.

2. Description of the Prior Art

The hydroxylation of phenol, substituted phenols or phenol ethers using hydrogen peroxide to prepare diphenols, substituted diphenols or alkoxyphenols is a reaction that is known to this art.

French Patent FR No. 2,071,464 describes a process in which the reaction is catalyzed by a strong acid, such as, for example, perchloric acid or sulfuric acid.

German Patent No. 2,410,742 describes a process similar to the above, in which the hydrogen peroxide is used in the form of a virtually anhydrous organic solution.

These two processes have considerable merit and the first is carried out industrially.

However, for several years attempts have been made to catalyze the hydroxylation reaction with solids that are not dissolved in the reaction mixture, in order to simplify their separation therefrom, enable the optional recycling thereof and to avoid salt-type byproducts which most often form during the removal of the dissolved acid catalysts.

Thus, French Patent FR No. 2,489,816 describes the use of titanium silicalite as a heterogeneous catalyst for the hydroxylation of aromatic compounds with hydrogen peroxide.

In fact, such catalysis is extremely difficult to reproduce. Moreover, the fine size of the catalyst particles renders their separation from the reaction mixture very difficult and their recycling problematical. In this latter regard, it will be appreciated that it is essential to be able to recycle a costly catalyst in an industrial process.

To overcome this problem of the separation of the catalyst, published European Patent Application No. 200,260 describes using agglomerates of these fine particles of titanium silicalite.

The difficulty in controlling safety in plants where hydrogen peroxide is used and the relative mediocrity of the yields of the prior art processes have provided the impetus for those skilled in the art to attempt to introduce a hydroxyl group directly onto an aromatic nucleus in the absence of any peroxide derivative. Such attempts, however, have to date been unsuccessful.

Moreover, the direct hydroxylation of an aromatic compound bearing no substituents or containing a deactivating substituent, such as benzene or the halogenobenzenes, is essentially absent from the scientific literature.

Thus, the only publication thought to describe the direct introduction of a hydroxyl group onto a benzene ring is an article by Iwamoto in the *Journal of Physical Chemistry*, 87, 6 (1983).

This reaction for the hydroxylation of benzene is carried out using nitrous oxide (N₂O) in the presence of a catalyst based on an oxide of a metal of Groups V or VI of the Periodic Table.

Vanadium oxide is the preferred oxide from among the oxides of metals of Groups V and VI of the Periodic Table. It is preferable to use this oxide in the presence of a support based on silica, in an amount by weight ranging from 1% to 10% relative to the support. The support preferably is silica, as alumina causes the formation of a mixture of carbon oxides in the majority of cases.

The Iwamoto process has attracted considerable interest, but the use of the catalysts described militates against conducting the process on an industrial scale.

Hence, serious need continues to exist in this art for a hydroxylation process that is applicable to a wide variety of aromatic substrates and which does not require employing hydrogen peroxide.

SUMMARY OF THE INVENTION

Accordingly, a major object of the present invention is the provision of an improved process for the direct hydroxylation of aromatic substrates which conspicuously avoids those disadvantages and drawbacks to date characterizing the state of this art.

Briefly, the present invention features hydroxylation of an aromatic compound of formula (I):

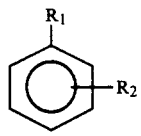

(I)

in which $R_1$ is an OH group, a bromine atom, a chlorine atom, a fluorine atom, a hydrogen atom, a straight or branched chain alkyl radical having from 1 to 6 carbon atoms, a straight or branched chain alkoxy radical having from 1 to 6 carbon atoms, and $R_2$ is a hydrogen atom, a straight or branched chain alkyl radical having from 1 to 6 carbon atoms, or a straight or branched chain alkoxy radical having from 1 to 6 carbon atoms, comprising intimately conducting, at a temperature ranging from 250° C. to 500° C., the aromatic compound of formula (I) with nitrous oxide, in the presence of a modified zeolite (a) or (b):

(a) a modified zeolite of ZSM-5 type having the general formula (II), expressed in terms of the oxide ratios:

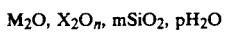

(II)

in which M is a cation selected from among hydrogen and the alkali metals, at least some of the M cations being a hydrogen atom; X is Ga, Fe, B, In, Cr, Sc, Co, Ni, Be, Zn, Cu, Sb, As or V; D is 2, 3 or 5, depending on the valency of the element X; m is a number greater than or equal to 20; and p is a number ranging from 0 to 40;

(b) a modified zeolite of ZSM-11 type having the general formula (III), expressed in terms of the oxide ratios:

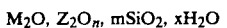

(III)

in which M is a cation selected from among hydrogen and the alkali metals, at least some of the cations M being a hydrogen atom; Z is Al, Ga, Fe, B, In, Cr, Sc, Co, Ni, Be, Zn, Cu, Sb, As or V; n is 2, 3 or 5, depending on the valency of the element Z; m is a number greater than or equal to 20; and x is a number ranging from 6 to 12.

DETAILED DESCRIPTION OF THE PREFERRED EMBODIMENTS OF THE INVENTION

More particularly according to the present invention, the modified zeolites of formula (II) or (III) may contain several of the elements represented by X or Z at the same time.

The modified zeolites of the ZSM-5 and ZSM-11 type of formula (II) or (III) which are typically used in the process of the invention are those in which the symbol X or the symbol Z more particularly represents the trivalent elements (Al, Ga, Fe, B, In, Cr and Sc) or divalent elements (Co, Ni, Be, Zn and Cu) indicated above, either alone or in combination with one another or in combination with the pentavalent elements indicated above (Sb, As and V).

The zeolites of the ZSM-5 type can be prepared by the process described in U.S. Pat. No. 3,702,888, replacing the aluminum compound by an inorganic gallium, iron, boron, indium, chromium, scandium, cobalt, nickel, beryllium, zinc, copper, antimony, arsenic or vanadium compound, or by a mixture of inorganic compounds of several of these elements.

The procedure entails preparing a solution containing tetraalkylammonium hydroxide, such as tetrapropylammonium hydroxide for example; sodium oxide; gallium oxide, iron oxide, boron oxide, indium oxide, chromium oxide, scandium oxide, cobalt oxide, nickel oxide, beryllium oxide, zinc oxide, copper oxide, antimony oxide, arsenic oxide or vanadium oxide, or a mixture of several of these oxides; silica and water. The solution contains oxide ratios in the following ranges:

(i) $OH^-/SiO_2$ from 0.07 to 10.0;
(ii) tetraalkylammonium/tetraalkylammonium $+Na^+$: from 0.2 to 0.95;
(iii) $H_2O/OH^-$: from 10 to 300;
(iv) $SiO_2/X_2O_n$ : greater than or equal to 20.

It is possible to use excess tetraalkylammonium hydroxide, which increases the $OH^-/SiO_2$ ratio indicated above. However, the excess hydroxide does not participate in the reaction.

The treatment to produce crystals of zeolites generally entails heating the above mixture at a temperature of 100° C. to 200° C. for a period of time of a few hours to 60 days under autogenous pressure.

Preferably, the reaction conditions are ten hours to ten days at a temperature of 150° C. to 200° C. The crystals are then separated from the liquid by cooling it to ambient temperature, filtering off the crystals obtained and then washing them with water.

The zeolite is then dried at about 100° C., in general for several hours. The preparation of zeolites of the ZSM-5 type can be carried out using compounds which generate the necessary oxides.

Thus, it is possible to use gallium, iron, boron, indium, chromium, scandium, cobalt, nickel, beryllium, zinc, copper, antimony, arsenic or vanadium nitrates, sodium silicate, silica gels, silicic acid, sodium hydroxide, or mixtures of these various compounds with the corresponding oxides.

The zeolites of the ZSM-11 type can be prepared by the process described in U.S. Pat. No. 3,709,979, if necessary replacing the aluminum compound by an inorganic gallium, iron, boron, indium, chromium, scandium, cobalt, nickel, beryllium, zinc, copper, antimony, arsenic or vanadium compound, or by a mixture of inorganic compounds of several of these elements.

It is thus possible to use the procedure described above for the zeolites of the ZSM-5 type, preparing a solution containing tetraalkylammonium oxide; sodium oxide; aluminum oxide, gallium oxide, iron oxide, boron oxide, indium oxide, chromium oxide, scandium oxide, cobalt oxide, nickel oxide, beryllium oxide, zinc oxide, copper oxide, antimony oxide, arsenic oxide or vanadium oxide or a mixture of several of these oxides; silica and water. The oxide ratios in this solution are in the following ranges:

(i) $Na_2O/SiO_2$: from 0.05 to 0.7;
(ii) tetraalkylammonium oxide/$SiO_2$: from 0.02 to 0.20;
(iii) $H_2O/Na_2O$ : from 50 to 800;
(iv) $SiO_2/Z_2O_n$ : greater than or equal to 20.

By the term "modified zeolite" are intended zeolites of the ZSM-5 and ZSM-11 type as defined above, in which at least some of the M cations are hydrogen and preferably the majority or all of the M cations are hydrogen.

This can be accomplished by treating the zeolites of the ZSM-5 and ZSM-11 type, in the formula of which the M cations are solely alkali metals or tetraalkylammonium ions, with an organic or inorganic acid.

Exemplary inorganic acids which may be used to acidify the zeolites are hydrochloric acid, sulfuric acid, nitric acid, perchloric acid and phosphoric acid.

Exemplary organic acids which may be used to acidify the zeolites are halosulfonic acids such as chlorosulfonic acid and fluorosulfonic acid, halomethanesulfonic acids such as trifluoromethanesulfonic acid, and halocarboxylic acids, such as trichloroacetic acid, dichloroacetic acid, monochloroacetic acid, trifluoroacetic acid, difluoroacetic acid, monofluoroacetic acid and monobromoacetic acid.

In a preferred embodiment, the acidification of the zeolite of the ZSM-5 or ZSM-11 type is effected by charging therethrough 10 cc to 100 cc of acid, having a normality of 0.1 N to 2 N, per gram of zeolite.

A throughput of this type can be carried out in a single step or, preferably, in several successive steps.

In the formulae (II) and (III) of the modified zeolites of the ZSM-5 and ZSM-11 type, the cation M which possibly does not represent hydrogen is preferably sodium.

Modified zeolites of the ZSM-5 and ZSM-11 types can also be obtained by exchanging all or some of the alkali metals using a solution of an inorganic ammonium salt, such as, for example, ammonium nitrate, ammonium fluoride or ammonium chloride, followed by a heat treatment for a few hours at temperatures of 300° C. to 800° C. in a stream of dry air in order to create $H^+$ sites.

According to the present invention, zeolites of the ZSM-5 types of formula (II) and of the ZSM-11 type of formula (III) in which the $SiO_2/X_2O_n$ or $SiO_2/Z_2O_n$ ratio ranges from 20 to 500 are preferred.

More preferably, this $SiO_2/X_2O_n$ or $SiO_2/Z_2O_n$ ratio in the formulae (II) and (III) ranges from 40 to 300.

It is desirable to carry out a treatment of the modified zeolites of the ZSM-5 and ZSM-11 type in order to improve their catalytic activity in the reaction of the hydroxylation of aromatic compounds of formula (I), using nitrous oxide.

This activation can entail, in particular, carrying out a heat treatment of the modified zeolites at a temperature of 300° C. to 800° C., and preferably of 400° C. to 700° C., for a few hours in a stream of dry inert gas such as nitrogen. If appropriate, the heat treatment can be continued for a few hours at a temperature in the ranges indicated above, but under a stream of dry air.

The modified zeolites of the ZSM-5 and ZSM-11 type can be used in various forms in the process of the invention: powder, in particular in laboratory tests, or shaped articles, such as granules (for example cylinders or beads), beads, pellets or monoliths (blocks in honeycomb form), which are produced by extrusion, molding, compacting, or any other known process.

In practice, on an industrial scale, it is the granule, bead and monolith forms which are the most advantageous, both with regard to effectiveness and with regard to convenience in handling.

As the process of the invention is carried out in vapor phase, the problem of the recovery of the catalyst is thus resolved.

Exemplary of the compounds of formula (I), particularly representative are fluorobenzene, phenol, benzene, toluene, orthocresol, metacresol, paracresol, anisole, bromobenzene, chlorobenzene, orthochlorophenol and parachlorophenol.

Phenol, fluorobenzene and benzene are compounds of formula (I) which are especially suited for hydroxylation by the process of the invention.

The nitrous oxide is used in the pure form, or as a mixture with an inert gas which does not contain oxygen, such as nitrogen.

The compound of formula (I) is preferably introduced as a mixture with the nitrous oxide, in a molar ratio of nitrous oxide relative to the compound of formula (I) of from 1 to 10.

In a preferred embodiment of the invention, the compound (I) is vaporized, mixed with nitrous oxide in the previously defined proportions and the mixture is circulated over the zeolites of formula (II) or (III). The reaction preferably is carried out at a temperature of from 300° to 500° C.

The gases produced from the reaction and containing, where appropriate, a mixture of isomers, are condensed and separated by any technique known to this art.

When it is applied to phenol, the process of the invention is particularly valuable since it permits the three dihydroxybenzenes, pyrocatechol, hydroquinone and resorcinol to be produced, while the known processes for the hydroxylation of phenol produce almost exclusively a pyrooateohol/hydro-quinone mixture. The process, therefore, provides an original route to resorcinol.

In order to further illustrate the present invention and the advantages thereof, the following specific examples are given, it being understood that same are intended only as illustrative and in nowise limitative.

EXAMPLE 1

Preparation of a gallium-containing zeolite of the ZSM-5 type

A solution of 5.94 g of gallium nitrate hydrate (Ga(NO$_3$)$_3$·6H$_2$O) and 16 g of H$_2$SO$_4$ (96%) in 200 g of water was poured into a solution of 200 g of sodium silicate (SiO$_2$/Na$_2$O=3.22) in 200 g of water.

24 g of tetrapropylammonium bromide in 100 g of water were added to the gel thus obtained.

The mixture was stirred for several minutes and the mixture was then placed in a stirred 1-liter autoclave, under autogenous pressure, for 4 days at 170° C.

The white solid thus obtained was filtered off, washed with water and dried at 100° C.

Analysis of the powder by X-ray diffraction confirmed the formation of a gallium-containing zeolite of the ZSM-5 type.

The SiO$_2$/Ga$_2$O$_3$ molar ratio was 80.

The activation of this gallium-containing zeolite entailed subjecting it to a heat treatment at 550° C. for 18 hours under a stream of dry nitrogen, then for 5 hours at 550° C. under a stream of dry air.

After cooling, the zeolite was subjected to ion exchange with a 1 M solution of NH$_4$NO$_3$ and to a heat treatment for 10 hours in a stream of dry air, in order to form H$^+$ sites.

EXAMPLE 2

Preparation of an iron-containing zeolite of the ZSM-5 type

A solution of 50 g of sodium metasilicate (Na$_2$SiO$_3$·5H$_2$O) in 50 g of water was poured into a solution containing 2.1 g of ferric nitrate (Fe(NO$_3$)$_3$·9H$_2$O) in 50 g of water.

The pH was adjusted to a highly acid value using 5.0 g of 96% H$_2$SO$_4$.

6.5 g of tetrapropylammonium bromide in 10 g of water were added to the gel obtained, which was pale lemon in color.

After vigorous stirring, the mixture was placed in a stainless steel autoclave, the autoclave was closed and the mixture was heated under autogenous pressure and with stirring for 5 days at 170° C.

The white solid obtained was filtered off, washed with water and dried at 100° C.

Analysis of the powder by X-ray diffraction confirmed the formation of an iron-containing zeolite of the ZSM-5 type.

The SiO$_2$/Fe$_2$O$_3$ molar ratio was 90.

Using the same operating method, iron-containing zeolites having SiO$_2$/Fe$_2$O$_3$ molar ratios of 120 and 150, respectively, were prepared by modifying the proportion of sodium metasilicate/ferric nitrate and adjusting the hydroxide content.

The activation of these iron-containing zeolites was carried out in the manner described in Example 1 to form the H$^+$ sites.

EXAMPLE 3

Preparation of a cobalt-containing zeolite of the ZSM-5 type

First, a solution A of 0.27 g of Co(NO$_3$)$_2$·6H$_2$O and 0.6 g of H$_2$SO$_4$ in 15 g of water was prepared.

Then a solution B of 10 g of silica (marketed under the trademark Q-Brand) in lo g of water and then a solution C of 1 g of tetrapropylammonium bromide in 10 g of water were prepared.

The solutions A and B were first mixed rapidly and stirred until a gel was obtained.

Solution C was then added to this gel, with gentle stirring.

The gel thus obtained was placed in a stirred autoclave for 3 days at 170° C.

The white solid obtained was filtered off, washed with water and dried at 100° C.

Analysis of the powder by X-ray diffraction confirmed the formation of a cobalt-containing zeolite of the ZSM-5 type.

The SiO$_2$/2CoO molar ratio was 80.

The activation of this cobalt-containing zeolite was carried out in the manner described in Example 1 to form the H+sites.

EXAMPLE 4

Preparation of an aluminum-containing zeolite of the ZSM-11 type

A solution A containing 55 g of sodium silicate (SiO$_2$/Na$_2$O = 3.22) and 1.3 g of 1,8-diaminooctane in 38 g of water was prepared.

A solution B containing 0.7 g of sodium aluminate in 40 g of water was prepared.

The two solutions A and B were mixed.

The pH of the gel thus obtained was adjusted to 1 using sulfuric acid.

The gel was placed in an autoclave, stirred for 3 days at 220° C.

The white solid obtained was filtered off, washed with water and dried at 100° C.

Analysis of the powder by X-ray diffraction confirmed the formation of aluminum-containing zeolite of the ZSM-11 type.

The SiO$_2$/Al$_2$O$_3$ molar ratio was 40.

The activation of this aluminum-containing zeolite was carried out in the manner described in Example 1 to form the H+sites.

EXAMPLES 5 to 10

Hydroxylation of fluorobenzene to fluorophenols

Experimental conditions (i) Vapor phase: continuous;
(ii) Catalyst: modified zeolite of the ZSM-5 or ZSM-11 type prepared in Examples 1, 2, 3 and 4 (see Table below);
(iii) Temperature: 400° C.;
(iv) Liquid space velocity/hour (weight of substrate/weight of catalyst/hour): 1.5 h$^{-1}$;
(v) Fluorobenzene/N$_2$/N$_2$O molar ratios: 2/5/8.

2 cc of modified zeolite (about 1 g) in powder form, dispersed in 4 cc of quartz in the form of grains (smaller than 0.8 mm) were introduced into a tubular reactor made of quartz and having a length of 16 cm and an internal diameter of 1.8 cm.

A bed of 10 cc of glass beads was then introduced into the reactor, enabling the gaseous mixture to homogenize.

The reactor thus charged was conditioned for 2 hours at 400° C. under nitrogen in a tubular oven.

The reaction was carried out continuously, introducing 1.5 cm$^3$/h of fluorobenzene, 1.44 l/h of N$_2$O and 0.9 l/h of nitrogen.

The results are reported in the Table below:

TABLE

| Examples | Modified zeolite | SiO$_2$/X$_2$O$_n$ or SiO$_2$/Z$_2$O$_n$ molar ratio | % DC of fluorobenzene | % Yld of fluorophenols |
|---|---|---|---|---|
| Example 5 | ZSM-5 Ga | 80 | 4.1 | 75 |
| Example 6 | ZSM-5 Co | 80 | 1.3 | 89 |
| Example 7 | ZSM-5 Fe | 90 | 16.0 | 90 |
| Example 8 | ZSM-5 Fe | 120 | 9.8 | 93 |
| Example 9 | ZSM-5 Fe | 150 | 8.4 | 94 |
| Example 10 | ZSM-11 Al | 40 | 1.2 | 69 |

% DC = degree of conversion
% Yld = yield relative to fluorobenzene converted

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a phenol, comprising directly reacting an aromatic compound of the formula (I):

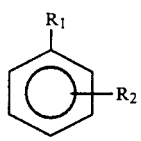

in which R$_1$ is an OH group, a bromine atom, a chlorine atom, a fluorine atom, a hydrogen atom, a straight or branched chain alkyl radical having from 1 to 6 carbon atoms, or a straight or branched chain alkoxy radical having from 1 to 6 carbon atoms, and R$_2$ is a hydrogen atom, a straight or branched chain alkyl radical having from 1 to 6 carbon atoms, or a straight or branched chain alkoxy radical having 1 to 6 carbon atoms, at a temperature of 250° C. to 500° C., with nitrous oxide, in the presence of a modified zeolite which comprises:

(a) a modified zeolite of ZSM-5 type of formula (II), expressed in terms of the oxide ratios thereof:

$$M_2O, X_2O_n, mSiO_2, pH_2O \quad (II)$$

in which M is a cation selected from among hydrogen and the alkali metals, at least some of the cations M being a hydrogen atom; X is Ga, Fe, B, In, Cr, Sc, Co, Ni, Be, Zn, Cu, Sb, As or V; D is 2, 3 or 5, depending on the valency of the element X; m is a number greater than or equal to 20; and p is a number ranging from 0 to 40, or (b) a modified zeolite of ZSM-11 type of general formula (III), expressed in terms of the oxide ratios thereof:

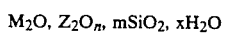

$$M_2O, Z_2O_n, mSiO_2, xH_2O \quad (III)$$

in which M is a cation selected from among hydrogen and the alkali metals, at least some of the cations M being a hydrogen atom; Z is Al, Ga, Fe, B, In, Cr, Sc, Co, Ni, Be, Zn, Cu, Sb, As or V; D is 2, 3 or 5, depending on the valency of the element Z; m is a number greater than or equal to 20; and x is a number ranging from 6 to 12.

2. The process as defined by claim 1, wherein said modified zeolites of ZSM-5 or ZSM-11 type, the symbol X or the symbol Z represents the trivalent elements (Al, Ga, Fe, B, In, Cr and Sc) or divalent elements (Co, Ni, Be, Zn and Cu), either alone or in combination with one another, or in combination with the elements Sb, As and/or V.

3. The process as defined by claim 1, said modified zeolites of ZSM-5 or ZSM-11 type having been prepared by treating a zeolite of ZSM-5 or ZSM-11 type, in the formula of which the cations M are only alkali metals or tetraalkylammonium ions, with an organic or inorganic acid.

4. The process as defined by claim 3, said zeolite having been treated with hydrochloric acid, sulfuric acid, nitric acid, perchloric acid or phosphoric acid.

5. The process as defined by claim 3, said zeolite having been treated with a halosulfonic acid, a halomethanesulfonic acid, or a halocarboxylic acid.

6. The process as defined by claim 1, wherein said modified zeolites of formulae (II) and (III), any cations M which are not hydrogen atoms are sodium atoms.

7. The process as defined by claim 1, said modified zeolites of formulae (II) and (III) having been prepared by ion exchange with a solution of an inorganic ammonium salt, followed by a heat treatment at temperatures of 300° C. to 800° C. in a stream of dry air to create the $H^+$ sites.

8. The process as defined by claim 1, wherein said modified zeolites of formulae (II) and (III), the $SiO_2/X_2O_n$ or $SiO_2/Z_2O_n$ ratio ranges from 20 to 500 are used.

9. The process as defined by claim 8, said $SiO_2/X_2O_n$ or $SiO_2/Z_2O_n$ ratio ranging from 40 to 300.

10. The process as defined by claim 1, said modified zeolites of formulae (II) and (III) having been heat treated at a temperature of 300° C. to 800° C. in a stream of dry inert gas.

11. The process as defined by claim 1, said compound of formula (I) comprising fluorobenzene, phenol, benzene, toluene, orthocresol, metacresol, paracresol, anisole, bromobenzene, chlorobenzene, orthochlorophenol or parachlorophenol.

12. The process as defined by claim 11, said compound of formula (I) comprising fluorobenzene, phenol or benzene.

13. The process as defined by claim 1, wherein the molar ratio of the nitrous oxide to the compound of formula (I) range from 1 to 10.

* * * * *